US010420582B2

(12) United States Patent
Kawaura et al.

(10) Patent No.: US 10,420,582 B2
(45) Date of Patent: Sep. 24, 2019

(54) PUNCTURE APPARATUS

(71) Applicant: TERUMO KABUSHIKI KAISHA, Tokyo (JP)

(72) Inventors: Masakatsu Kawaura, Sunnyvale, CA (US); Nao Mandai, Mountain View, CA (US); Nobuo Takahashi, Cupertino, CA (US); Thomas J. Fogarty, Portola Valley, CA (US); David Willis, Los Altos, CA (US); Thomas Howell, San Jose, CA (US); Peter Carlotto, San Jose, CA (US); Shuji Uemura, San Francisco, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 462 days.

(21) Appl. No.: 15/156,790

(22) Filed: May 17, 2016

(65) Prior Publication Data

US 2017/0014154 A1 Jan. 19, 2017

Related U.S. Application Data

(60) Provisional application No. 62/192,211, filed on Jul. 14, 2015.

(51) Int. Cl.
| | | |
|---|---|---|
| *A61B 17/34* | (2006.01) | |
| *A61B 17/02* | (2006.01) | |
| *A61B 17/06* | (2006.01) | |
| *A61B 17/062* | (2006.01) | |

(Continued)

(52) U.S. Cl.
CPC ...... *A61B 17/3403* (2013.01); *A61B 17/0218* (2013.01); *A61B 17/0625* (2013.01); *A61B 17/06109* (2013.01); *A61B 17/3468* (2013.01); *A61B 2017/00039* (2013.01);
(Continued)

(58) Field of Classification Search
CPC .... A61F 2/0004; A61F 2/0031; A61F 2/0036; A61F 2/0045; A61F 2/0063; A61B 17/0469; A61B 17/0482; A61B 17/3403
See application file for complete search history.

(56) References Cited

U.S. PATENT DOCUMENTS

| | | | |
|---|---|---|---|
| 6,911,003 B2 | 6/2005 | Anderson et al. | |
| 7,052,453 B2 * | 5/2006 | Presthus | A61F 2/0022 600/29 |

(Continued)

OTHER PUBLICATIONS

WO2013176098 Machine Translation.*

*Primary Examiner* — Carrie R Dorna
(74) *Attorney, Agent, or Firm* — Buchanan Ingersoll & Rooney PC

(57) ABSTRACT

A puncture apparatus is disclosed, which can include an insertion portion that is insertable into a living body, the insertion portion including an urethral insertion portion and a vaginal insertion portion, the urethral insertion portion and the vaginal insertion portion each having at least two sensors; a puncture needle that punctures living body tissues near the insertion portion in a state in which the insertion portion is inserted into the living body, the puncture needle having at least one sensor on a distal portion of the puncture needle; and a monitor configured to receive information relating to a positional relationship between a distal portion of the puncture needle and the insertion portion.

20 Claims, 12 Drawing Sheets

(51) Int. Cl.
*A61B 17/00* (2006.01)
*A61B 17/30* (2006.01)
(52) U.S. Cl.
CPC .............. *A61B 2017/00805* (2013.01); *A61B 2017/0608* (2013.01); *A61B 2017/306* (2013.01)

(56) References Cited

U.S. PATENT DOCUMENTS

| | | | |
|---|---|---|---|
| 8,147,397 B1* | 4/2012 | Witzmann | A61B 17/062 600/29 |
| 2010/0036384 A1* | 2/2010 | Gorek | A61B 17/7091 606/104 |
| 2015/0073465 A1 | 3/2015 | Ariura et al. | |
| 2015/0080644 A1 | 3/2015 | Kawaura et al. | |

* cited by examiner

PUNCTURE APPARATUS

CROSS-REFERENCES TO RELATED APPLICATIONS

This application claims priority to U.S. Provisional Patent Application No. 62/192,211 filed on Jul. 14, 2015, the entire content of which is incorporated herein by reference.

TECHNICAL FIELD

The present disclosure relates to a puncture apparatus, and more particularly to a sensor arrangement on an insertion instrument and a monitor configured to receive information relating to a positional relationship between a distal portion of a puncture needle and the insertion instrument, and wherein the insertion instrument includes a vaginal insertion portion (or vaginal stabilizer) and a urethral insertion portion (or urethral stabilizer).

BACKGROUND DISCUSSION

In a patient suffering from urinary incontinence, for example, stress urinary incontinence, urine leakage (involuntary urination) occurs due to an abnormal pressure exerted during a normal exercise or by, for example, laughing, coughing, or sneezing. This can be attributable, for example, to loosening of a pelvic floor muscle, which is a muscle for supporting a urethra, caused by childbirth.

For treatment of urinary incontinence, surgical therapy can be effective. For example, a tape-shaped implant called a "sling" can be placed indwelling in the body to support the urethra (for example, U.S. Pat. No. 6,911,003). In order to put a sling indwelling in the body, an operator incises a vagina with a surgical knife, dissects a biological tissue (living body tissue) between the urethra and the vagina, and provides communication between the exfoliated biological tissue site and an exterior through an obturator foramen by using a puncture needle. Then, in such a state, the sling is placed indwelling in the body.

If a vaginal wall is incised, however, there can be a fear that the sling might be exposed to an inside of the vagina via a wound caused by the incision. There can also be a fear that complications might occur which can be caused by an infection via the wound. In addition, since the vaginal wall is incised, an invasiveness of the procedure can be rather great and patient burden can be relatively heavy. In addition, there can be a fear that the urethra or the like can be damaged by a surgical knife in the course of the procedure by the operator, and there can be a fear that the operator himself might damage his fingertip by the surgical knife.

Further, when an implant is placed indwelling in a living body, there may arise a case, depending on a length of the implant, where part of the implant can located near the living body surface, such that the patient may experience pain.

SUMMARY

A puncture apparatus is disclosed which can relatively alleviate the burden exerted on a patient when an implant is placed indwelling in the living body.

A puncture apparatus is disclosed comprising: an insertion portion that is insertable into a living body, the insertion portion including an urethral insertion portion and a vaginal insertion portion, the urethral insertion portion and the vaginal insertion portion each having at least two sensors; a puncture needle that punctures living body tissues near the insertion portion in a state in which the insertion portion is inserted into the living body, the puncture needle having at least one sensor on a distal portion of the puncture needle; and a monitor configured to receive information relating to a positional relationship between a distal portion of the puncture needle and the insertion portion.

A method is disclosed of preventing a region of a living body from being punctured, comprising: inserting an insertion portion into a living body, the insertion portion comprising at least one of a urethral insertion portion that is inserted into a urethra and a vaginal insertion portion that is inserted into a vagina, the urethral insertion portion and the vaginal insertion portion each having at least two sensors; inserting a puncture needle that punctures living body tissues near the insertion portion in a state in which the insertion portion is inserted into the living body; detecting a positional relationship between a distal portion of the puncture needle and the insertion portion; and informing an operator of the positional relationship between the distal portion of the puncture needle and the insertion portion using a monitor.

DETAILED DESCRIPTION

Figure 1:
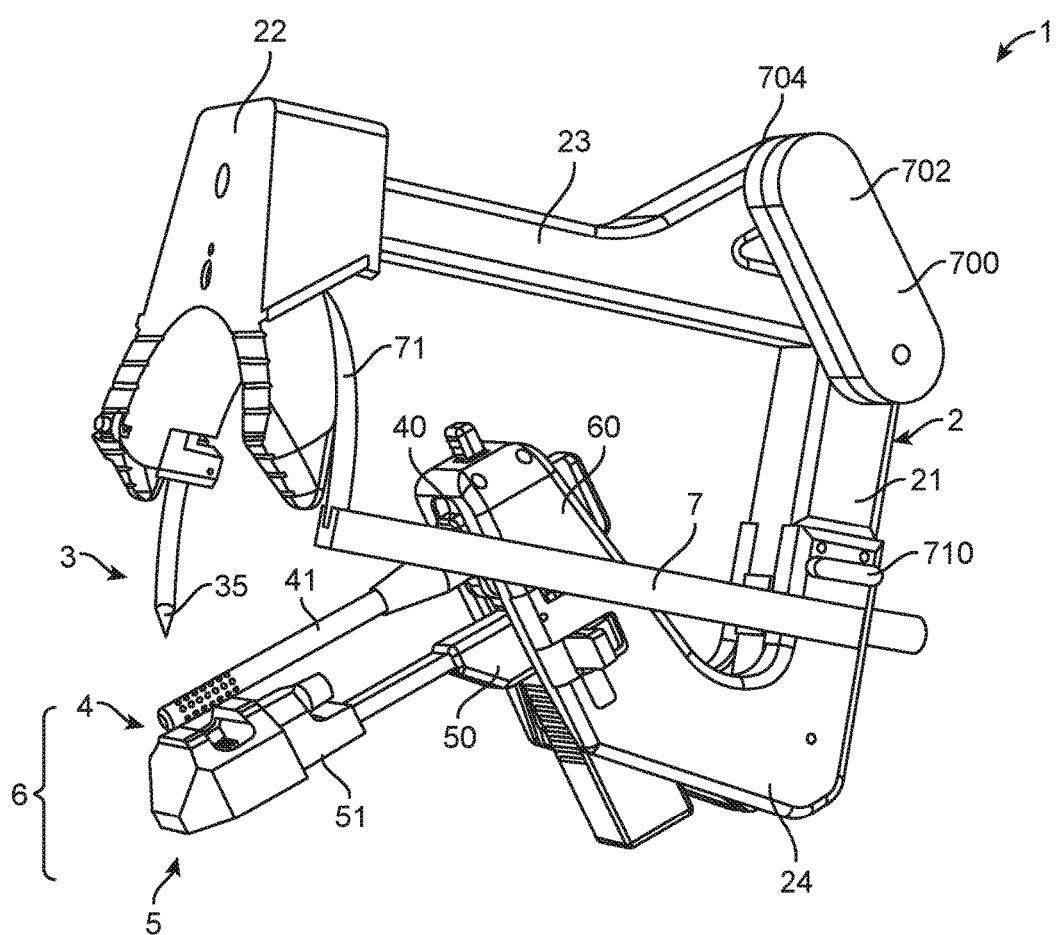
FIG. 1 is a perspective view showing a puncture apparatus to be used at a time of placing indwelling in a living body an implant according to an exemplary embodiment of the present disclosure.

FIGS. 1-5 are views showing a puncture apparatus 1 to be used at a time of placing indwelling in a living body an implant (not shown) according to exemplary embodiments of the present disclosure.

In accordance with an exemplary embodiment, a puncture apparatus 1 as shown in FIGS. 1-5 is an apparatus to be used for treatment of female urinary incontinence, for example, to be used in a process in which a biological tissue-supporting implant for treatment of urinary incontinence is embedded (implanted) into a living body as described in U.S. Patent Publication Nos. 2015/0080644 and 2015/0073465, which are incorporated herein by reference in their entirety.

The puncture apparatus 1 can include a frame (support unit) 2, a puncture member 3, a urethral insertion member 4, a vaginal insertion member 5, and an operating member 7. In the puncture apparatus 1, the urethral insertion member 4 and the vaginal insertion member 5 constitute an insertion instrument 6. The operating member 7 is a member operating the puncture member 3.

Such an operating member 7, as shown in FIGS. 1 to 5, can include an insertion portion 71, which is a portion to be inserted in the puncture member 3, and can function as a stylet that supports the puncture member 3 from the inside. With the insertion portion 71 inserted in the puncture member 3, the puncture member 3 is connected to the operating member 7, whereby it is enabled to operate the puncture member 3 by the operating member 7. Such an insertion portion 71 is in an arcuate shape corresponding to the shape of the puncture member 3. A center angle of the insertion portion 71 is set in conformity with a center angle of the puncture member 3. In accordance with an exemplary embodiment, a distal portion of the insertion portion 71 can be tapered off. The presence of the tapered distal portion can enable relatively smooth fitting of the puncture member 3 over the insertion portion 71 (smooth insertion of the insertion portion 71 into the puncture member 3).

In accordance with an exemplary embodiment, the insertion portion 71 can be circular in cross-sectional shape. Alternatively, the insertion portion 71 may be flat-shaped in cross section. The flat shape is not limited. Examples of the flat shape applicable here can include not only ellipses but also rounded-cornered rhombuses, rounded-cornered rectangles (flat shapes), and spindle-like shapes enlarged (enlarged in diameter) at a central portion as compared with both end portions of the insertion portion being flat-shaped in cross section.

In accordance with an exemplary embodiment, such an operating member 7 can be configured to be higher than the puncture member 3 in rigidity. The material constituting the operating member 7 is not limited. Examples of the material applicable here can include various metallic materials such as stainless steels, aluminum, aluminum alloys, titanium, and titanium alloys.

The puncture member 3 is a member puncturing a living body. Such a puncture member 3 can include, for example, an elongate sheath (medical tube) (not shown), and a needle body provided at a distal end of the sheath as described in U.S. Patent Publication Nos. 2015/0080644, which is incorporated herein by reference in its entirety. For example, the sheath main body (not shown) can be configured by use of an elongate tube, which is open at a distal end and a proximal end of the elongate tube. Such a sheath main body can have an internal space in which an implant main body can be inserted. In addition, the sheath main body can be in an arcuate curved shape, and can have a flat cross-sectional shape.

In accordance with an exemplary embodiment, for example, the puncture member 3 passes through the living body from one groin to the other groin. A sheath for introducing the sling into the living body can be connected at the distal end of the puncture member 3 which is protruded out of the living body. The sheath can be placed into the living body by moving in the opposite direction to the direction of introducing the puncture member 3.

The frame 2 turnably holds the operating member 7 on which the puncture member 3 is mounted. In addition, the frame 2 detachably fixes the insertion instrument 6. The frame 2 has a function of determining a puncture route for the needle body 35 at the time of puncturing of a biological tissue by the puncture member 3. For example, the frame 2 can determine a positional relationship between the puncture member 3, the urethral insertion member 4, and the vaginal insertion member 5 in such a manner that when a biological tissue is punctured by the puncture member 3, the needle body (or puncture needle) 35 can pass between the urethral insertion member 4 and the vaginal insertion member 5 without colliding against or striking any of the insertion members 4 and 5.

As shown in FIGS. 1-5, the frame 2 can include a bearing portion 21, a guide portion (holding portion) 22 guiding the puncture member 3, an interlock portion 23 interlocking the bearing portion 21 and the guide portion 22 to each other, and a fixing portion 24 to which the insertion instrument 6 is fixed.

The bearing portion 21 can be located on the proximal end in the puncture apparatus 1. The guide portion 22 can be located on the distal end in the puncture apparatus 1, and is disposed opposite to the bearing portion 21. As shown in FIGS. 1-5, the guide portion 22 is formed with a roughly C-shaped guide groove (not shown) accommodating the puncture member 3 and guiding the puncture member 3.

Figure 2:
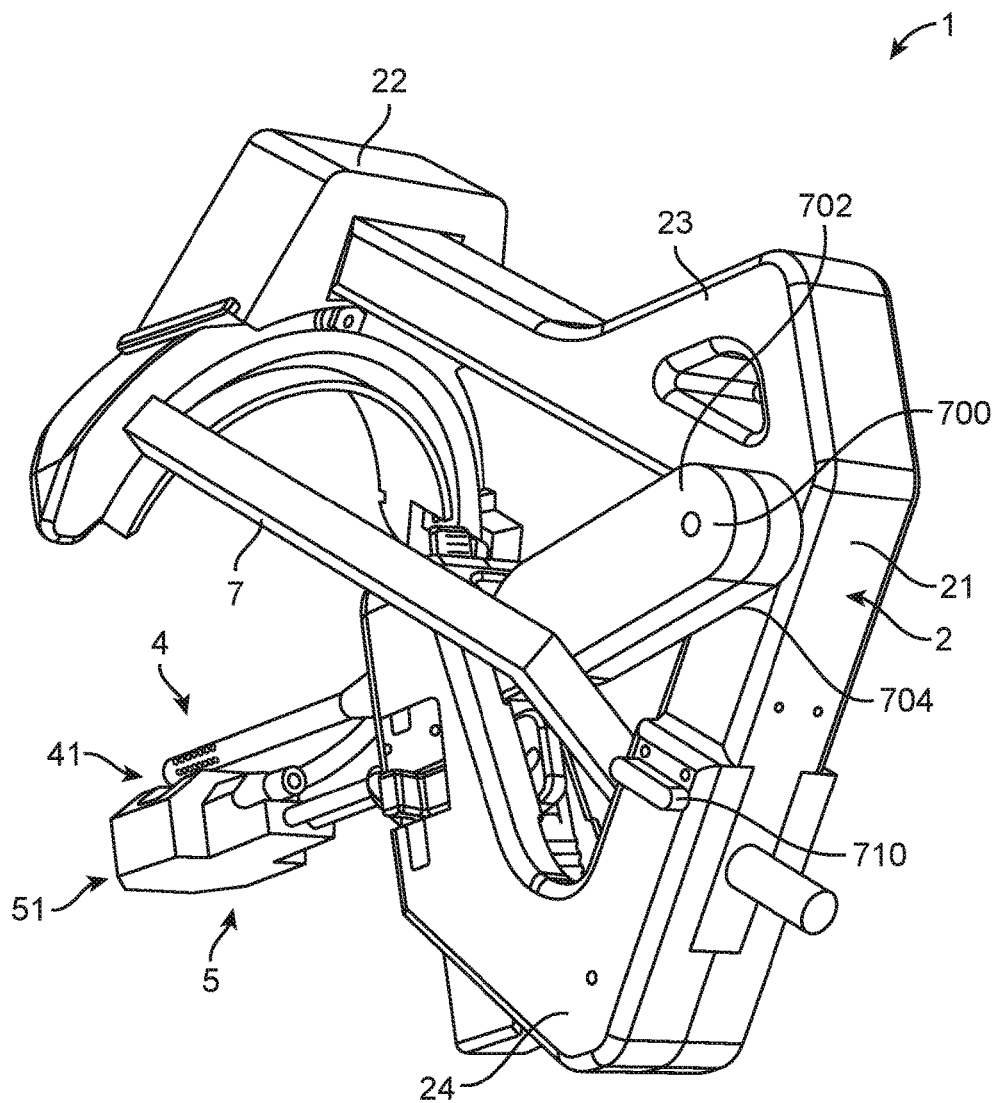
FIG. 2 is another perspective view showing a puncture apparatus to be used at a time of placing indwelling in a living body an implant according to an exemplary embodiment of the present disclosure.
Figure 3:
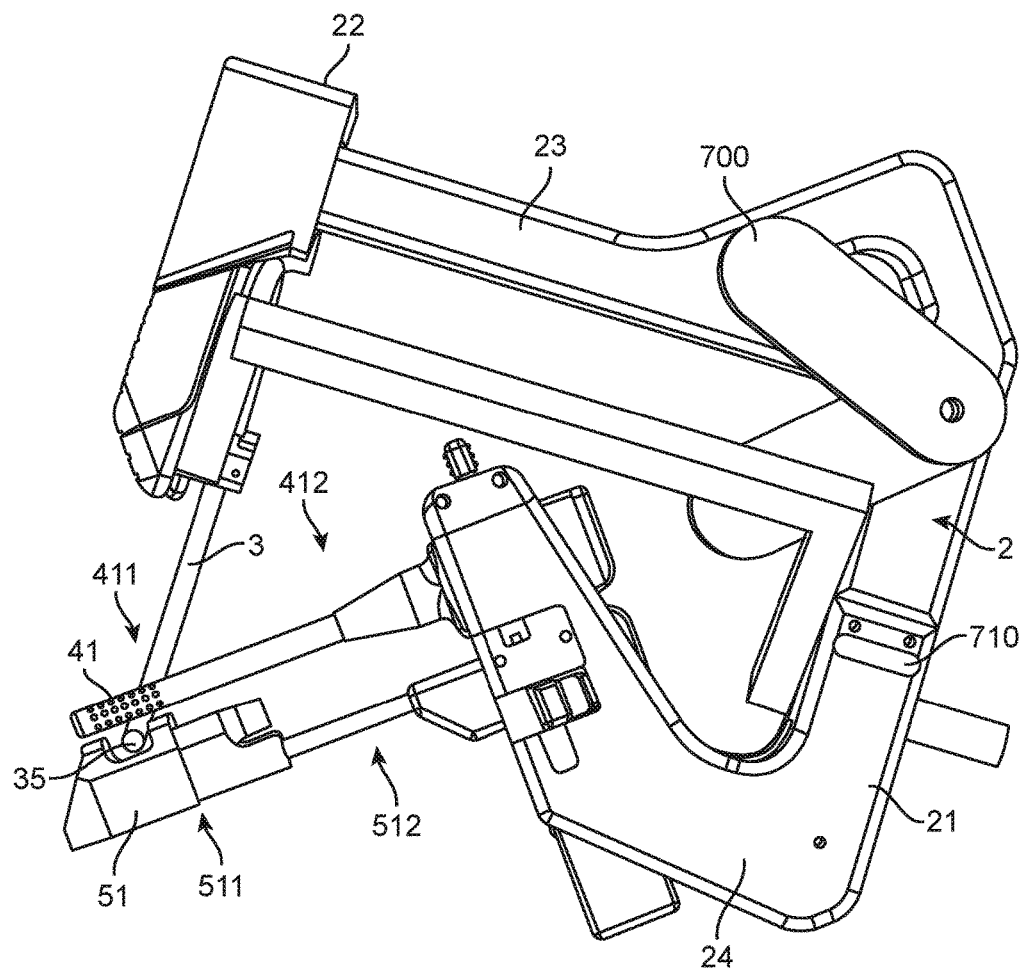
FIG. 3 is a perspective view showing a puncture apparatus to be used at a time of placing indwelling in a living body an implant according to an exemplary embodiment of the present disclosure.
Figure 4:
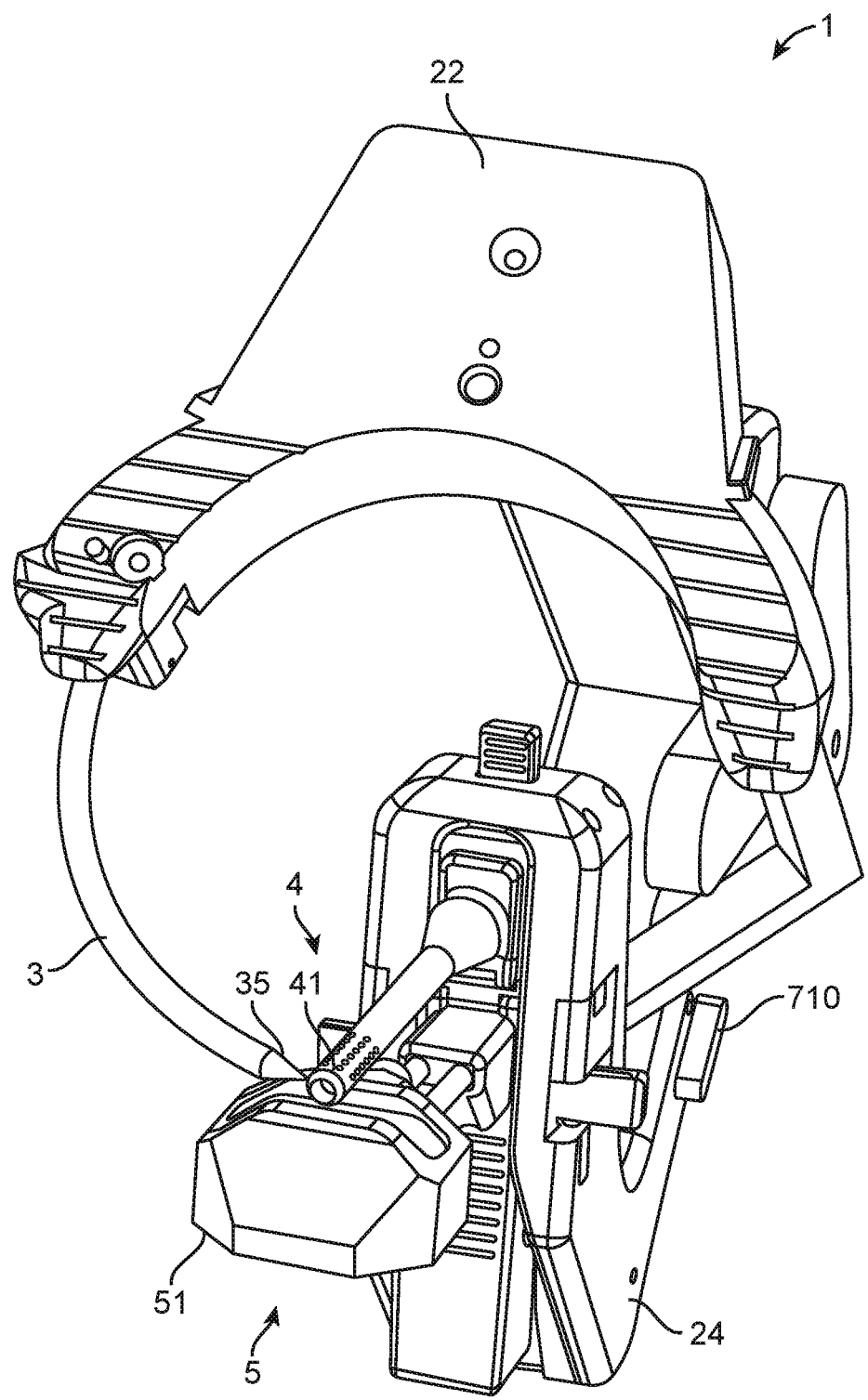
FIG. 4 is a perspective view showing a puncture apparatus to be used at a time of placing indwelling in a living body an implant according to an exemplary embodiment of the present disclosure.
Figure 5:
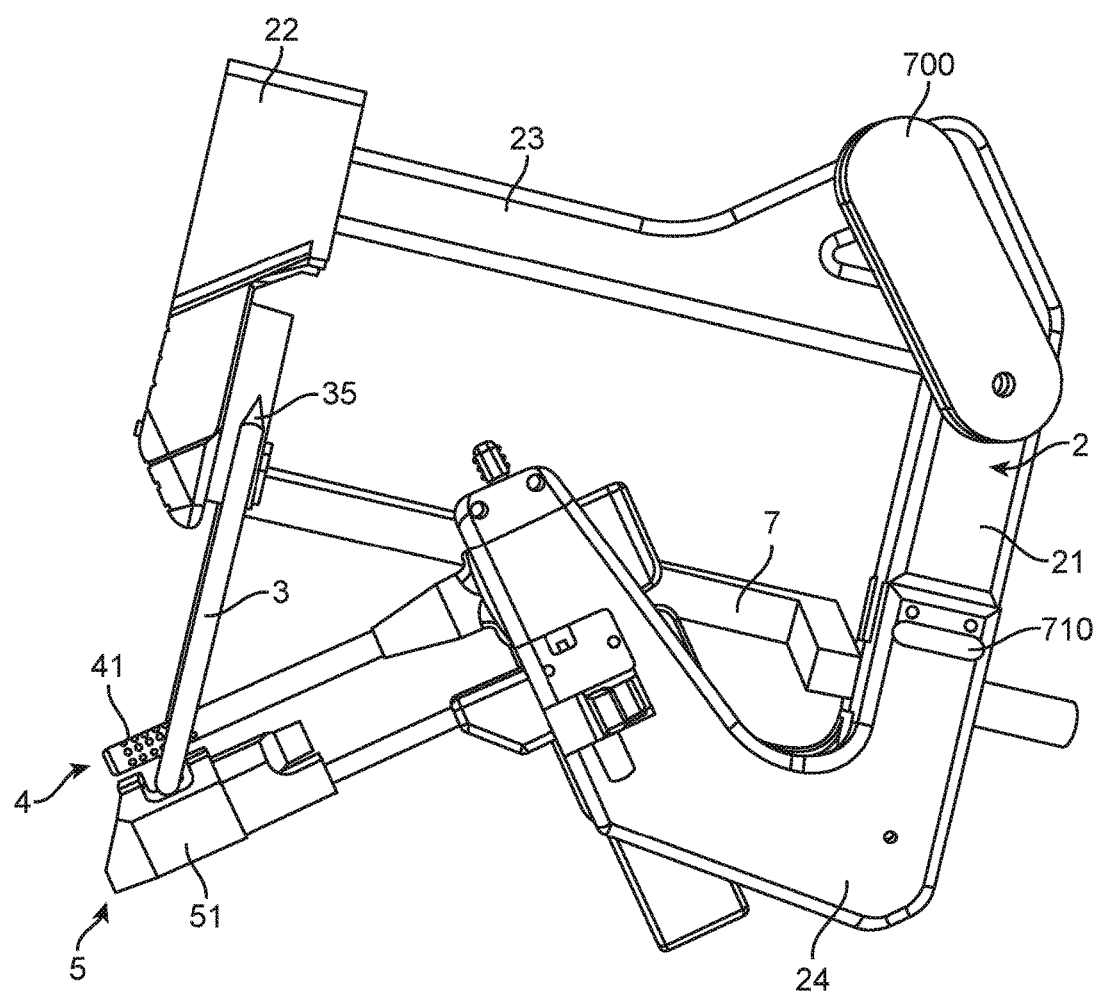
FIG. 5 is a perspective view showing a puncture apparatus to be used at a time of placing indwelling in a living body an implant according to an exemplary embodiment of the present disclosure.

When a rotating operation is applied to the operating member 7 as shown in FIGS. 2-5, the puncture member 3 gradually protrudes from the guide portion 22, and, the needle body 35 enters into the guide portion 22 via a proximal end opening. In accordance with an exemplary embodiment, the puncture apparatus 1 can include a stop plate (or needle stopper) 700, which can be used to control the movement of the operating member 7 and the puncture member 3 during use. In accordance with an exemplary embodiment, the stop plate 700 helps prevent the needle body 35 from piercing the puncture target (or site) as shown in FIGS. 2 and 3. Once the stop plate 700 is rotated upward as shown in FIGS. 1, 4, and 5, the operating member 7 and the puncture member 3 can continue forward into and through the puncture target (or site), which is positioned between the vaginal insertion member (or vaginal stabilizer) 51 and the urethral insertion member (or urethral stabilizer) 41. As shown in FIGS. 1-5, the stop plate 700 can be rotatably attached to the frame 2 in the path of the operating member 7 on which the puncture member 3 is mounted. The apparatus 1 can also include an adjustment knob 710 (FIGS. 1-5 and 15). The adjustment knob 710 allows the operator to adjust the position of the fixing portion 24 in an up and down and forward and backward direction relative to bearing portion 21, the guide portion 22, and the interlock portion 23. Thus, by adjusting the relative position of the fixing portion 24 to the bearing portion 21, the guide portion 22, and the interlock portion 23, the position of the urethral insertion member 4 and vaginal insertion member 5 relative to the puncture member 3 can be changed and adjusted as needed.

The interlock portion 23 can interlock the shaft portion 21 and the guide portion 22 to each other. In addition, the interlock portion 23 can be in the shape of a bar. The interlock portion 23 can also function as a grasping portion, allowing an operator to use the puncture apparatus 1 while grasping the interlock portion 23.

As shown in FIGS. 1-5, the insertion instrument 6, which can include a urethral insertion member (second insertion portion) 41 to be inserted into a urethra, a vaginal insertion member (first insertion portion) 51 to be inserted into a vagina, and a support portion 60 supporting the urethral insertion portion 41 and the vaginal insertion portion 51. As disclosed above, the insertion instrument 6 can be composed essentially of the urethral insertion member 4 and the vaginal insertion member 5. The urethral insertion member 4 can have the urethral insertion portion 41, and the vaginal insertion member 5 can have the vaginal insertion portion 51.

In addition, the support portion 60 can include a support portion 40, which is possessed by the urethral insertion member 4 and supports the urethral insertion portion 41, and a support portion 50, which is possessed by the vaginal insertion member 5 and supports the vaginal insertion portion 51. In the insertion instrument 6, the urethral insertion member 4 and the vaginal insertion member 5 can be freely detachable by way of the support portions 40 and 50, respectively. The urethral insertion member 4 and the vaginal insertion member 5 will be sequentially described below.

As shown in FIGS. 1-5, the urethral insertion member 4 can include the elongated urethral insertion portion 41 whose portion ranging from a distal end to an intermediate portion of insertion portion 41 is to be inserted into a urethra, and the support portion 40, which supports the urethral insertion portion 41. In the following, for convenience of description as shown in FIG. 3, that portion of the urethral insertion member 4 which is located inside the urethra (inclusive of a bladder) in the mounted state will be referred to also as "insertion portion 411" whereas that portion of the urethral insertion member 4 which is exposed via a urethra orifice to the outside of the body in the mounted state and which ranges to the support portion 40 will be referred to also as "non-insertion portion 412."

The vaginal insertion member 5 can include the elongated vaginal insertion member (first insertion portion) 51 whose portion from a distal end to an intermediate portion of insertion portion 51 is inserted into a vagina, and the support portion 50 supporting the vaginal insertion portion 51. In the following, for convenience of description as shown in FIG. 3, that portion which is located in the vagina in the mounted state will be referred to also as the "insertion portion 511," and that portion which is exposed via a vaginal orifice to the outside of the body in the mounted state and which ranges to the support portion 50 will be referred to also as "non-insertion portion 512."

The vaginal insertion portion 51 can be elongated. In accordance with an exemplary embodiment, the vaginal insertion portion 51 is spaced from the urethral insertion portion 41 on the distal end. In accordance with an exemplary embodiment, the insertion portion 511 can be parallel or inclined relative to the insertion portion 411. In the mounted state, for example, the puncture apparatus 1 can be held stably onto the patient, and burden on the patient is mitigated. The inclination angle of the vaginal insertion portion 511 relative to the urethral insertion portion 411 is not limited, for example, the inclination angle can be about 0 to 45 degrees, and more preferably about 0 to 30 degrees, or alternatively, most preferably about 0 degrees as shown in FIGS. 1-5.

Figure 6:
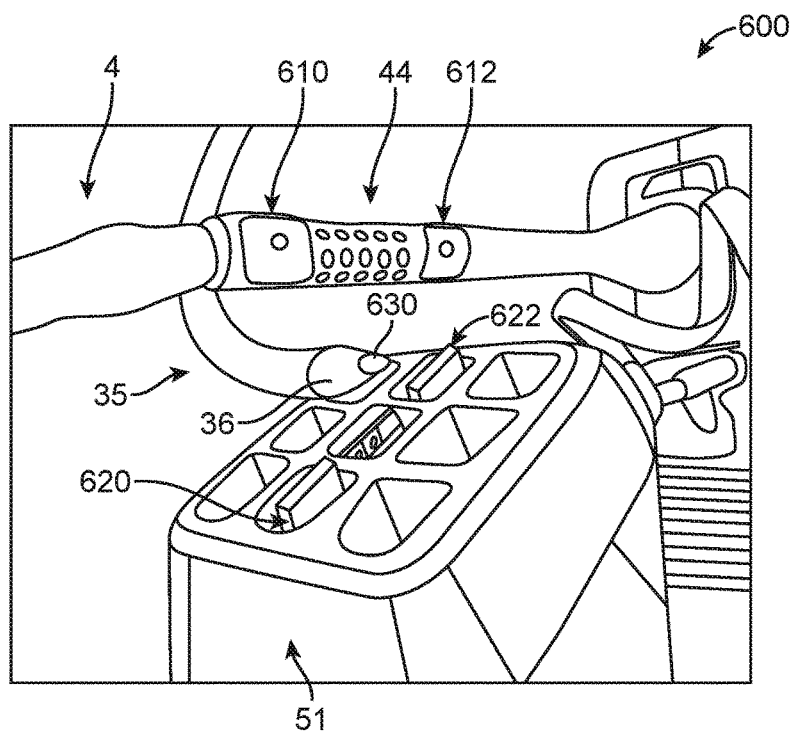
FIG. 6 is a perspective view of a sensor arrangement, which includes a vaginal insertion portion, a urethral insertion portion, and a needle tip in accordance with an exemplary embodiment.

FIG. 6 is a perspective view of a sensor arrangement 600, which includes a pair of sensors 620, 622 on the vaginal insertion portion 51, a pair of sensors 610, 612 on the urethral insertion portion 41, and a magnet 630 on the needle tip 36 of the needle body 35. In accordance with an exemplary embodiment, the urethral insertion portion 41 can include a pair of sensor 610, 612, which can be positioned on proximal side and a distal side of the plurality of suction holes 44 at an intermediate portion of the urethral insertion portion. As shown in FIG. 6, the plurality of suction holes 44 can be laid out over the whole range in the circumferential direction of the urethral insertion portion 41. Each of the suction holes 44 can be connected to a suction port 45 provided at a proximal portion of the urethral insertion portion 41, via the inside of the urethral insertion portion 41. The pair of sensors 610, 612 can be a pair of magnetic sensors, for example, a pair of hall sensors, which are transducers that can vary their output voltage in response to a magnetic field.

In addition, the vaginal insertion portion 51 can also include a pair of sensors, 620, 622, which are preferably positioned within or on an upper surface the vaginal insertion portion 51 and immediately below the pair of sensors 610, 612 on the urethral insertion portion 41. The pair of sensors 620, 622 can be a pair of magnetic sensors, for example, a pair of hall sensors, which are transducers that can vary their output voltage in response to a magnetic field. The needle tip 36 can include a magnet 630, which passes through the four sensors 610, 612, 620, 622 during puncturing of the target site (or target tissue).

Figure 7:
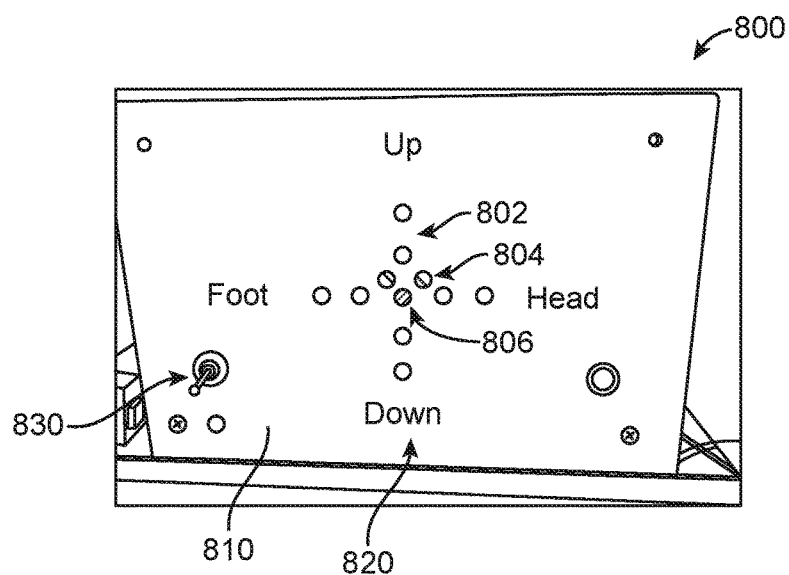
FIG. 7 is a front view of a monitor in accordance with an exemplary embodiment.

FIG. 7 is a front view of a monitor 800 in accordance with an exemplary embodiment. As shown in FIG. 7, the monitor 800 can include a plurality of lights 810, which can include, for example, red 802, yellow 804, and green 806 lights. The monitor 800, for example, can include a single green light 806, which is surrounded by a four pairs of red lights 802 and a pair of yellow lights 804. In accordance with an exemplary embodiment, the pair of yellow lights 804 is located just above the single green light. Each of the pairs of red light 802 extend outward from the green light 806 at the twelve, 3, 6, and 9 o'clock positions, respectively. In addition, to assist the operator with directions during use, the monitor can include terminology 820 such as "up", "down", "head", and "foot". The monitor 800 can also include an ON and OFF switch or button 830. In accordance with an exemplary embodiment, the monitor 800 can be attached to a computer having a processor and Operating System (OS) and/or the monitor 800 includes a processor and Operating System (OS).

Figure 8:
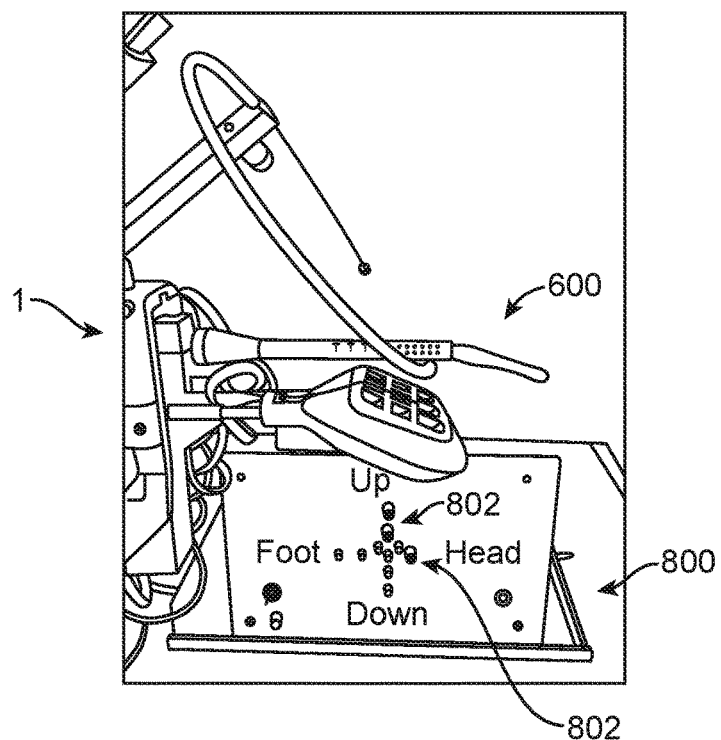
FIG. 8 is an example of the sensor arrangement showing on the monitor that the needle tip is too high.

FIG. 8 is an example of the sensor arrangement 600 showing on the monitor 800 that the needle tip 36 is too high. For example, as shown in FIG. 8, if the needle tip 36 is too high, for example, too close to the urethral insertion portion 41, the two red lights 802 at the 12 o'clock position on the monitor 800 will be illuminated. If the needle tip 36 is too low, for example, too close to the vaginal insertion portion 51, the two red lights 802 at the 6 o'clock position on the monitor 800 will be illuminated. If the needle tip 36 is too close to the head of the patient, the two red lights 802 at the 3 o'clock position on the monitor 800 will be illuminated. If the needle tip 36 is too close to the foot of the patient, the two red lights 802 at the 9 o'clock position on the monitor 800 will be illuminated.

Figure 9:
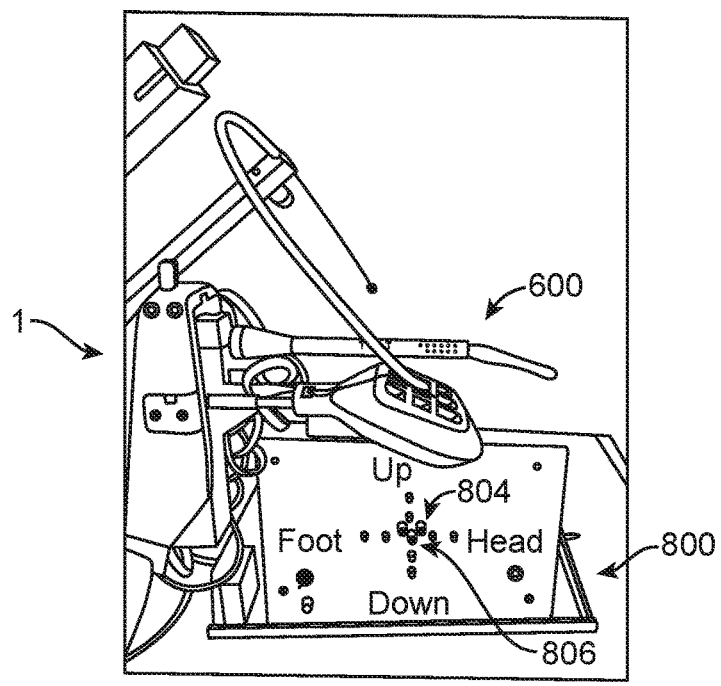
FIG. 9 is an example of the sensor arrangement showing on the monitor that the needle tip is on a predefined needle pass.

FIG. 9 is an example of the sensor arrangement 600 showing on the monitor that the needle tip is on a predefined needle pass. As shown in FIG. 9, if the needle tip 36 is on the correct or predetermined path, the green light 806 and/or two yellow lights 804 immediately above the green light 806 will be illuminated.

Next, one example, of the use of the puncture apparatus 1 will be described with reference to FIGS. 10-18. Here, the description will describe the procedure showing the use of a stop plate (or needle stopper) 700 in use with a sensor arrangement 600 in accordance with an exemplary embodiment. In accordance with an exemplary embodiment, the stop plate 700 can be composed of at least a first part or section 702, and a second part of section 704, which are configured to overlap each other. (FIGS. 1 and 2). The first and second parts 702, 704 can move independently of each other, which allow the operator the ability to change the rotational distance of the operating member 7 based on which part or section 702, 704 of the stop plate 700 is used to stop the rotational movement of the operating member 7.

As set forth above, when a rotational operation is applied to the operating member 7 as shown in FIGS. 2-5, the puncture member 3 gradually protrudes from the guide portion 22, and, the needle body 35 enters into the guide portion 22 via a proximal end opening. In accordance with an exemplary embodiment, the puncture apparatus 1 can include a stop plate (or needle stopper) 700, which can be used to control the movement of the puncture member 3 during use. In accordance with an exemplary embodiment, the stop plate 700 prevents the needle body 35 from piercing the puncture target (puncture site) until the stop plate 700 rotates upward as shown in FIGS. 1, 4, and 5, which allows the puncture member 3 to continue forward into and through the puncture target (puncture site).

Figure 10:
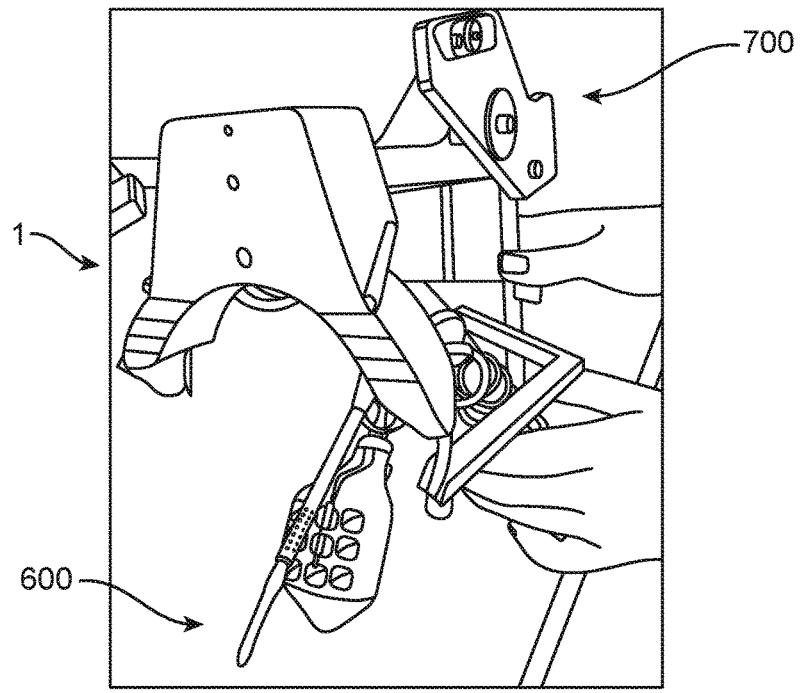
FIG. 10 is a diagram explaining a step of the procedure when the puncture apparatus illustrated in FIGS. 1-9 showing the use of a needle stopper in accordance with an exemplary embodiment.
Figure 11:
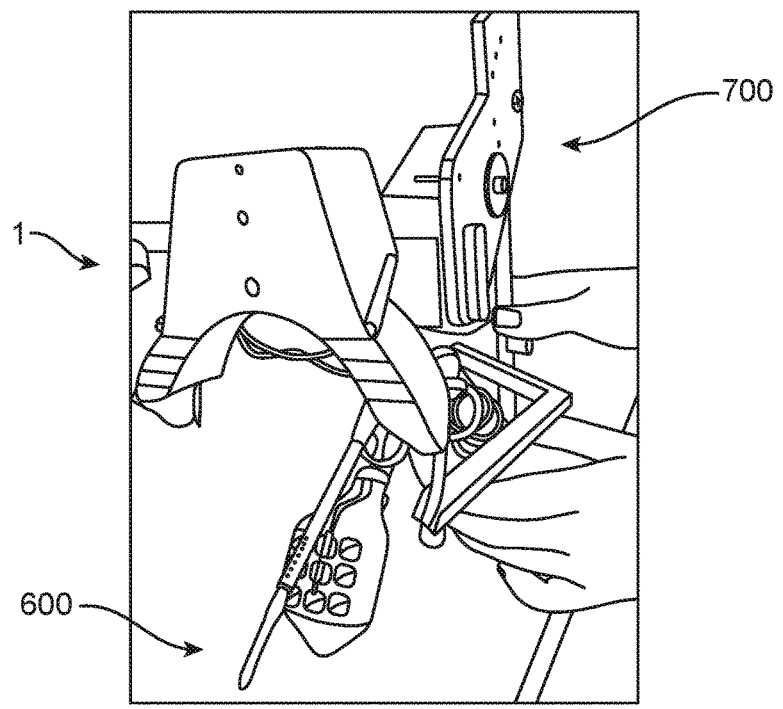
FIG. 11 is a diagram explaining a step of the procedure when the puncture apparatus illustrated in FIGS. 1-9 showing the use of a needle stopper in accordance with an exemplary embodiment.

As shown in FIGS. 10 and 11, the puncture apparatus 1 is prepared for use and the stop plate 700 is rotated downward. The rotation of the stop plate 700 downward can help prevent the needle body 35 from piercing the puncture target until the stop plate 700 is rotated upward as disclosed herein.

As disclosed in U.S. Patent Publication Nos. 2015/0080644 and 2015/0073465, which are incorporated herein by reference in their entirety, the patient is prepared for the puncture apparatus 1 is set to the use state. For example, the puncture apparatus 1 is set to a state in which the puncture apparatus is put on the body surface. In addition, the puncture apparatus 1 is set to a state in which the urethral insertion portion 41 is inserted into a urethra (not shown) and the vaginal insertion portion 51 is inserted into a vagina (not shown). The balloon (not shown) is inserted into the bladder in the deflated state and a balloon inflation device such as a syringe not illustrated is connected to the port. Then, a working fluid supplied from the balloon inflation device is sent to the inside of the balloon via the lumen to inflate the balloon. Due to this, the inflated balloon catches on the bladder neck and thereby the position of the urethral-insertion portion relative to the bladder and the urethra can be fixed.

Figure 12:
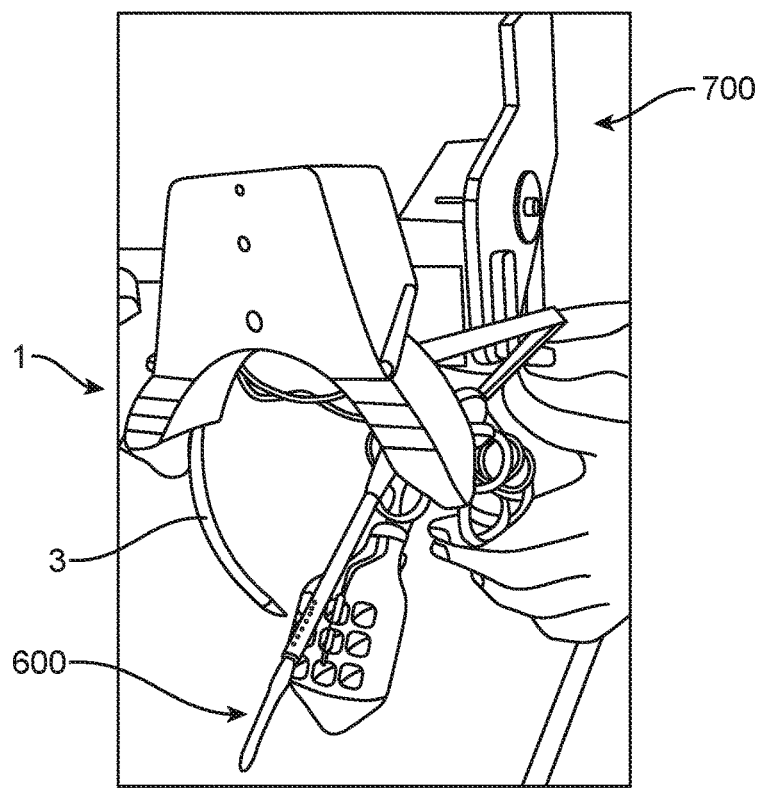
FIG. 12 is a diagram explaining a step of the procedure when the puncture apparatus illustrated in FIGS. 1-9 showing the use of a needle stopper in accordance with an exemplary embodiment.
Figure 13:
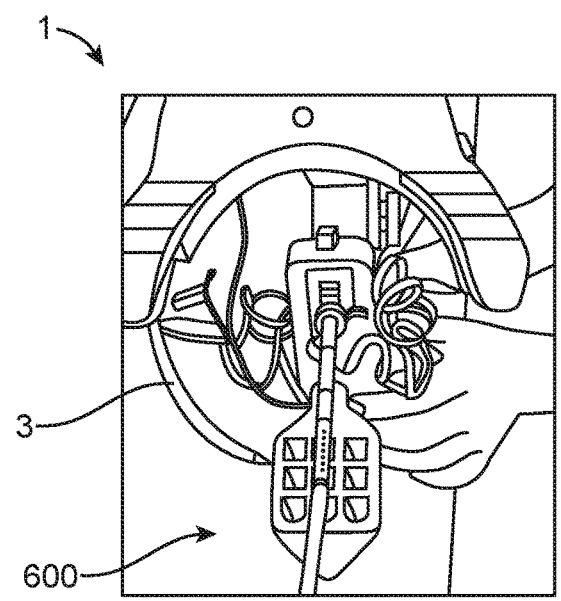
FIG. 13 is a diagram explaining a step of the procedure when the puncture apparatus illustrated in FIGS. 1-9 showing the use of a needle stopper in accordance with an exemplary embodiment.

Next, as illustrated in FIGS. 12 and 13, the needle body 35 in the assembled state is inserted into a through-hole (not shown), the needle body 35 can be thrust directly, and the rotary movement operation of the puncture needle can be carried out. In accordance with an exemplary embodiment, as the needle body 35 is thrust into the through-hole, the needle tip 36 stops before puncturing the puncture target via the stop plate 700.

Figure 14:
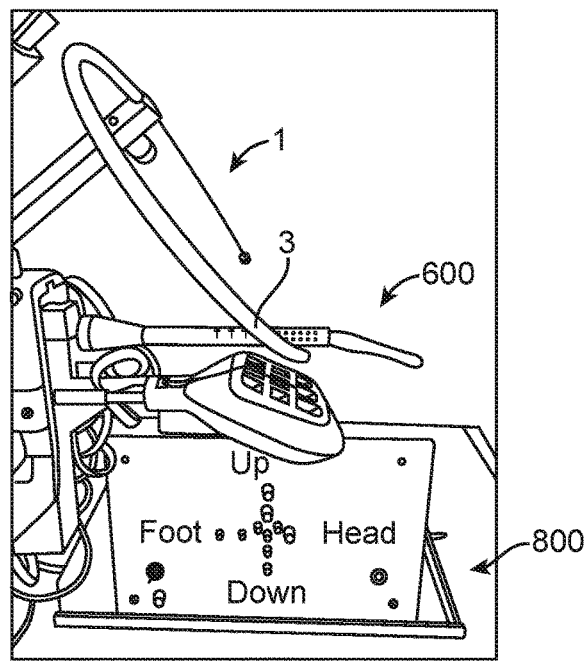
FIG. 14 is a diagram explaining a step of the procedure when the puncture apparatus illustrated in FIGS. 1-9 showing the use of a needle stopper in accordance with an exemplary embodiment.

In addition, as shown in FIG. 14, the magnet 630 on the needle tip 36 in combination with the sensors 610, 612, 620, 622 (FIG. 6) on the urethral insertion portion 41 and the vaginal insertion portion 51 provides a signal to the monitor 800, which can provide the operator with an indication of the relative position of the needle tip 36 to the urethral insertion portion 41 and the vaginal insertion portion 51.

Figure 15:
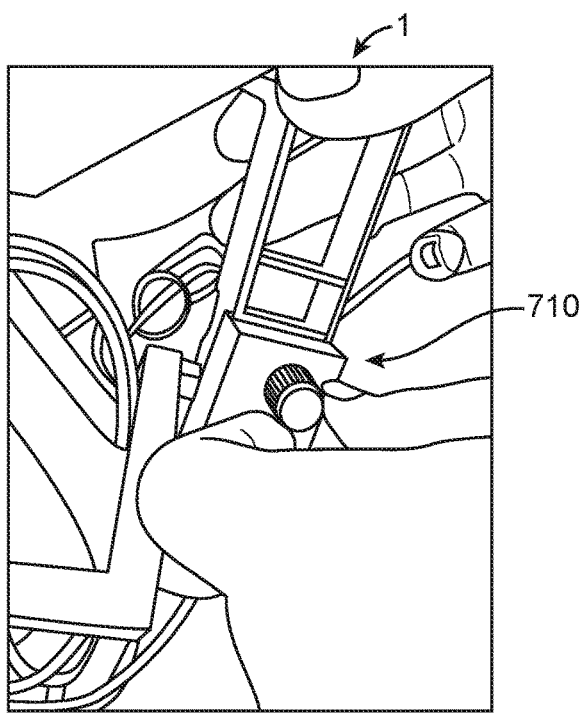
FIG. 15 is a diagram explaining a step of the procedure when the puncture apparatus illustrated in FIGS. 1-9 showing the use of a needle stopper in accordance with an exemplary embodiment.
Figure 16:
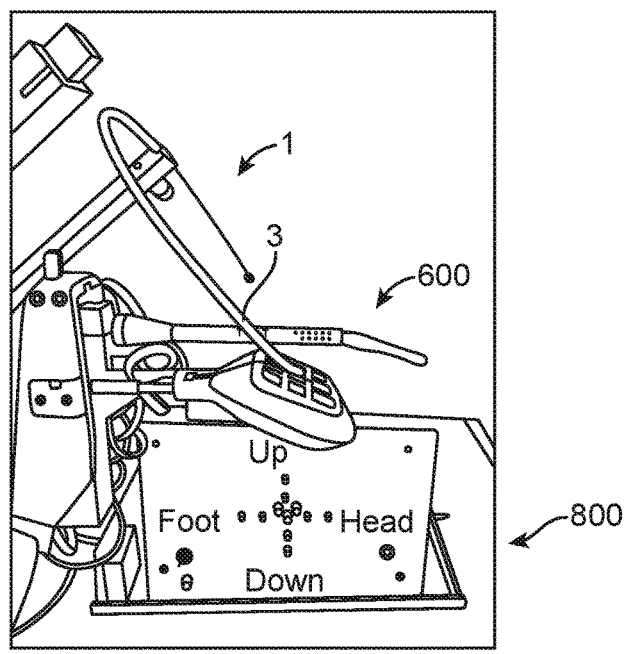
FIG. 16 is a diagram explaining a step of the procedure when the puncture apparatus illustrated in FIGS. 1-9 showing the use of a needle stopper in accordance with an exemplary embodiment.

If needed, as shown in FIGS. 15 and 16, the relative position of the needle tip 36 to the urethral insertion portion 41 and the vaginal insertion portion 51 can be adjusted using the adjustment knob 710.

Figure 17:
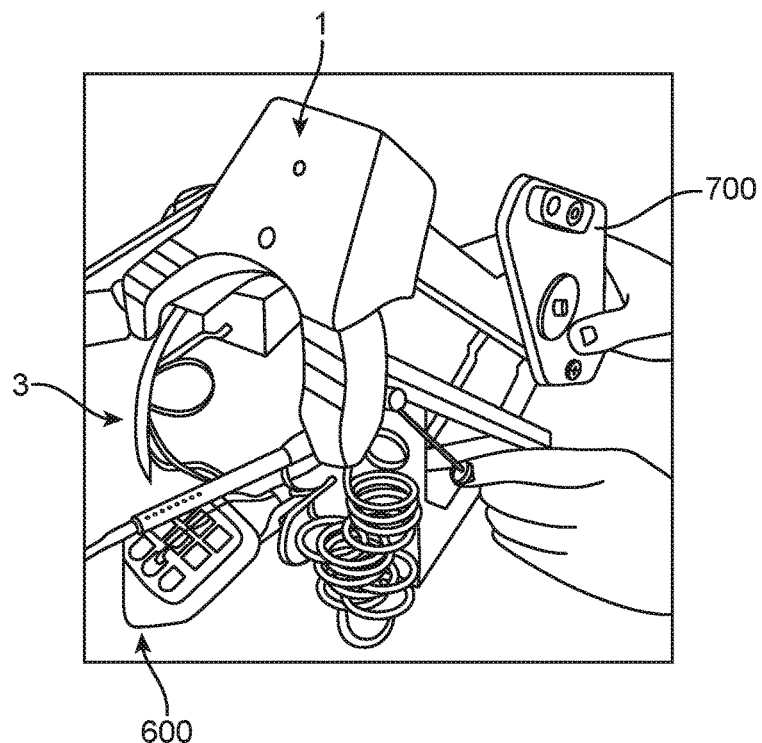
FIG. 17 is a diagram explaining a step of the procedure when the puncture apparatus illustrated in FIGS. 1-9 showing the use of a needle stopper in accordance with an exemplary embodiment.
Figure 18:
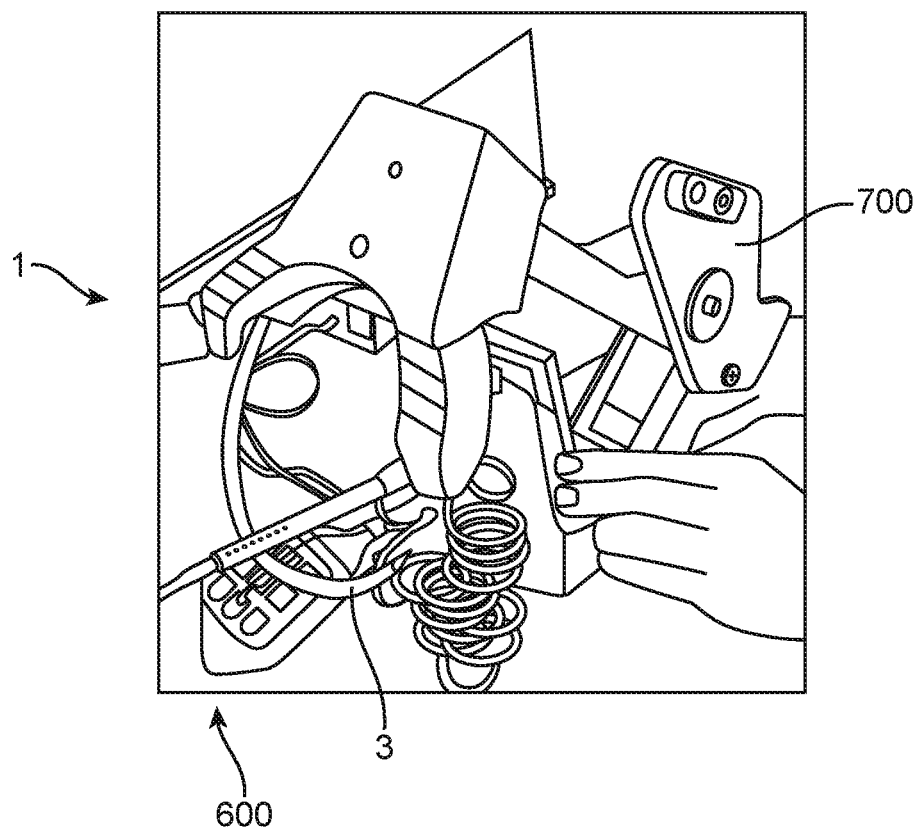
FIG. 18 is a diagram explaining a step of the procedure when the puncture apparatus illustrated in FIGS. 1-9 showing the use of a needle stopper in accordance with an exemplary embodiment.

Once the relative position of the needle tip 36 has been confirmed to pass through the target site, the stop plate 700 can be raised, and the needle tip 36 can continue through the target site as shown in FIGS. 17 and 18.

In addition, while the case where the puncture apparatus 1 is applied to an implant for treatment of female urinary incontinence has been described in the above exemplary embodiments, this is not restrictive of the use of the implant.

Examples of which the present disclosure is applicable can include pelvic floor diseases inclusive of excretory disorders (urinary urgency, frequent urination, urinary incontinence, fecal incontinence, urinary retention, dysuria, etc.), pelvic organ prolapse, vesicovaginal fistula, urethrovaginal fistula, and pelvic pain, which would be attendant on weakening of the group of pelvic floor muscles. The pelvic organ prolapse include such diseases as cystocele, enterocele, rectocele, and hysterocele, or such diseases as anterior vaginal prolapse, posterior vaginal prolapse, vaginal apical prolapse, and vaginal vault prolapse, which are denominations based on classification of the vaginal wall part being prolapsed.

In addition, examples of overactive tissue can include the bladder, vagina, uterus, and bowels. Examples of lessactive tissue can include bones, muscles, fascias, and ligaments. For example, in relation to the pelvic floor diseases, examples of the lessactive tissue include obturator fascia, coccygeus fascia, cardinal ligament, uterosacral ligament, and sacrospinous ligament.

Examples of the procedure for interlocking an overactive tissue in the pelvic floor disorder with the lessactive tissue, can include a retropubic sling surgery, a transobturator sling surgery (Transobturator Sling Surgery, Transobturator Tape; TOT), a tension-free vaginal mesh (Tension-free Vaginal Mesh; TVM) surgery, a uterosacral ligament suspension (Uterosacral Ligament Suspension; USLS) surgery, an iliococcygeus fascia fixation surgery, and a coccygeus fascia fixation surgery.

The detailed description above describes a puncture apparatus. The disclosure is not limited, however, to the precise exemplary embodiments and variations described. Various changes, modifications and equivalents can effected by one skilled in the art without departing from the spirit and scope of the disclosure as defined in the accompanying claims. It is expressly intended that all such changes, modifications and equivalents which fall within the scope of the claims are embraced by the claims.

What is claimed is:

1. A puncture apparatus, the puncture apparatus comprising:
   an insertion member that is insertable into a living body, the insertion member including a urethral insertion member and a vaginal insertion member, the urethral insertion member and the vaginal insertion member each having at least two sensors, the at least two sensors on each of the urethral insertion member and the vaginal insertion member being arranged such that a sensor is on a distal portion of the urethral insertion member and an other sensor is proximal to the sensor on the distal portion of the urethral insertion member, and a sensor is on a distal portion of the vaginal insertion member and an other sensor is proximal to the sensor on the distal portion of the vaginal insertion member, and wherein the at least two sensors on each of the urethral insertion member and the vaginal insertion member define a target tissue to be punctured;
   a puncture needle that is adapted to puncture living body tissues near the insertion member in a state in which the insertion member is inserted into the living body, the puncture needle having at least one sensor on a distal portion of the puncture needle;
   an adjustment device configured to adjust a positional relationship between the distal portion of the puncture needle and the insertion member; and
   a monitor configured to receive information relating to the positional relationship between the distal portion of the puncture needle and the insertion member.

2. The puncture apparatus according to claim 1, wherein the urethral insertion member has a plurality of suction holes, the at least two sensors of the urethral insertion member being on a distal side and a proximal side of a plurality of suction holes of the urethral insertion member.

3. The puncture apparatus according to claim 2, wherein the at least two sensors of the vaginal insertion member are within or on an upper surface the vaginal insertion member and immediately below the at least two sensors on the urethral insertion member.

4. The puncture apparatus according to claim 1, wherein the at least two sensors of the urethral insertion member and the at least two sensors of the vaginal insertion member are hall sensors.

5. The puncture apparatus according to claim 4, wherein the at least one sensor on the distal portion of the puncture needle is a magnet.

6. The puncture apparatus according to claim 1, wherein the urethral insertion member is adapted to be inserted into a urethra and has an elongated shape, and the vaginal insertion member is adapted to be inserted into a vagina and has an elongated shape.

7. The puncture apparatus according to claim 1, wherein the monitor has a plurality of lights, the plurality of lights including a plurality of red lights and at least one green light, the plurality of red lights and the at least one green light providing an indication to an operator of the positional relationship between the distal portion of the puncture needle and the insertion member.

8. The puncture apparatus according to claim 7, wherein the at least one green light is surrounded by the at least two red lights, the at least two red lights being four pairs of red lights, each pair of red lights arranged outward from the green light at twelve, 3, 6, and 9 o'clock positions.

9. The puncture apparatus according to claim 1, wherein the puncture needle is curved into a shape of a circular arc; and
   the puncture apparatus has a support member that supports the puncture needle rotationally movably around a center axis of the circular arc, and a guide member configured to accommodate and guide the puncture needle.

10. The puncture apparatus according to claim 9, wherein the support member is configured to determine a positional relationship between the puncture needle, the urethral insertion member, and the vaginal insertion member in such a manner that when a biological tissue is punctured by the puncture needle, the puncture needle passes between the urethral insertion member and the vaginal insertion member without colliding against or striking the urethral insertion member and the vaginal insertion member.

11. The puncture apparatus according to claim 9, further comprising:
   a stop plate rotatably attached to the support member in a path of an operating member, the operating member configured to rotatably move the puncture needle, and wherein the stop plate is configured to prevent the puncture needle from piercing the target tissue until the stop plate is moved from the path of the operating member.

12. The puncture apparatus according to claim 1, wherein the adjustment device is configured to move the puncture needle in an upward direction and a downward direction or a forward direction and a rearward direction relative to the urethral insertion member and vaginal insertion member.

13. A method of preventing a region of a living body from being punctured, the method comprising:
   inserting an insertion member into a living body, the insertion member including a urethral insertion member that is inserted into a urethra and a vaginal insertion member that is inserted into a vagina, the urethral insertion member and the vaginal insertion member each having at least two sensors, the at least two sensors on each of the urethral insertion member and the vaginal insertion member being arranged such that a sensor is on a distal portion of the urethral insertion member and an other sensor is proximal to the sensor on the distal portion of the urethral insertion member, and a sensor is on a distal portion of the vaginal insertion member and an other sensor is proximal to the sensor on the distal portion of the vaginal insertion member, and wherein the at least two sensors on each of the urethral insertion member and the vaginal insertion member define a target tissue to be punctured;
   inserting a puncture needle that punctures living body tissues near the insertion member in a state in which the insertion member is inserted into the living body, the puncture needle having at least one sensor on a distal portion of the puncture needle;
   detecting a positional relationship between the distal portion of the puncture needle and the insertion member;

informing an operator of the positional relationship between the distal portion of the puncture needle and the insertion member using a monitor; and adjusting the positional relationship between the distal portion of the puncture needle and the insertion member by changing the positional relationship of the distal portion of the puncture needle relative to the urethral insertion member and the vaginal insertion member.

14. The method according to claim 13, comprising:

positioning the at least two sensors of the urethral insertion member on a distal side and a proximal side of a plurality of suction holes of urethral insertion member.

15. The method according to claim 14, comprising:

positioning the at least two sensors of the vaginal insertion member within or on an upper surface the vaginal insertion member and immediately below the at least two sensors on the urethral insertion member.

16. The method according to claim 13, wherein the at least two sensors of the urethral insertion member and the at least two sensors of the vaginal insertion member are hall sensors.

17. The method according to claim 16, wherein the at least one sensor on the distal portion of the puncture needle is a magnet.

18. The method according to claim 13, comprising:

arranging a plurality of lights on the monitor, the plurality of lights including a plurality of red lights and at least one green light, the plurality of red lights and the at least one green light providing an indication to an operator of the positional relationship between the distal portion of the puncture needle and the urethral insertion member and the vaginal insertion member.

19. The method according to claim 13, wherein the puncture needle is curved into a shape of a circular arc; and the puncture apparatus has a support member that supports the puncture needle rotationally movably around a center axis of the circular arc, and a guide member configured to accommodate and guide the puncture needle.

20. The method according to claim 19, wherein the support member is configured to determine a positional relationship between the puncture needle, the urethral insertion member, and the vaginal insertion member in such a manner that when a biological tissue is punctured by the puncture needle, the puncture needle passes through the target tissue and between the urethral insertion member and the vaginal insertion member without colliding against or striking the urethral insertion member and the vaginal insertion member.

* * * * *